United States Patent [19]
Cardin et al.

[11] Patent Number: 5,861,383
[45] Date of Patent: Jan. 19, 1999

[54] SULFATED POLYSACCHARIDE FRACTIONS HAVING ANTI-HIV ACTIVITY

[75] Inventors: Alan D. Cardin; Richard L. Jackson, both of Cincinnati, Ohio

[73] Assignee: Merrell Pharmaceuticals Inc., Cincinnati, Ohio

[21] Appl. No.: 707,354

[22] Filed: Sep. 4, 1996

Related U.S. Application Data

[63] Continuation of Ser. No. 435,775, May 5, 1995, abandoned, which is a continuation of Ser. No. 190,820, Feb. 2, 1994, abandoned, which is a division of Ser. No. 1,370, Jan. 7, 1993, abandoned, which is a division of Ser. No. 821,130, Jan. 14, 1992, Pat. No. 5,272,261, which is a continuation of Ser. No. 375,795, Jul. 5, 1989, abandoned, which is a continuation-in-part of Ser. No. 295,856, Jan. 11, 1989, abandoned.

[51] Int. Cl.$^6$ .................... A61K 31/715; A61K 31/725
[52] U.S. Cl. .................. 514/56; 514/54; 514/57; 514/58; 514/59; 514/60
[58] Field of Search ................... 14/56, 54, 57, 14/58, 59, 60

[56] References Cited

U.S. PATENT DOCUMENTS

| | | | |
|---|---|---|---|
| 4,119,774 | 10/1978 | Anderson et al. | 536/21 |
| 4,783,446 | 11/1988 | Neushul | 514/54 |
| 4,840,941 | 6/1989 | Ueno et al. | 514/59 |
| 4,966,894 | 10/1990 | Herr et al. | 514/56 |
| 5,053,398 | 10/1991 | Mori et al. | 514/54 |
| 5,055,457 | 10/1991 | Schrinner et al. | 514/59 |

FOREIGN PATENT DOCUMENTS

| | | |
|---|---|---|
| 0232744 | 8/1987 | European Pat. Off. . |
| 0292663 | 11/1988 | European Pat. Off. . |
| 0293826 | 12/1988 | European Pat. Off. . |
| 0342544 | 11/1989 | European Pat. Off. . |
| 3734962 | 5/1989 | Germany . |
| 69204909 | 4/1992 | WIPO . |

OTHER PUBLICATIONS

Carré et al. Biochimica et Biophysica Acta 1995, 1243, 175–180.
Hirose, et al., Biochemistry, vol. 26, pp. 5505–5512 (1987).
Cardin, et al., Arteriosclerosis, vol. 9(1):21–32, Jan./Feb. 1989.
Rusche, Proc. Natl. Acad. Sci, USA, vol. 85, pp. 3198–3202, May 1988.
Griffith, et al., Biophys. Res. Commun. 83(3):1198–1205 (1978).
Bianchini, et al., J. Pharm. Exp. Ther. 220(2):406–410 (1982).
Suzuki, et al., The EMBO Journal 4(10):2519–2524 (1985).
Ito, et al., Antiviral Res. 7:361–367 (Jun. 1987).
Nakashima, et al., Jpn. J. Cancer Res. 78:1164–1168 (Nov. 1987).
Yamamoto, et al., Arch of AIDS Res., 1:45–56 (1987).
Mitsuya, et al., Science 240:646–649 (Apr. 1988).
Tochikura, et al., Virology 164:542–546 (Jun. 1988).
Rusche, et al., Chemical Abstracts 190:21281b (Jul. 1988).
Baba, et al., PNAS (USA) 85:6132–6136 (Aug. 1988).
Yoshida, et al., Biochem. Pharmacol. 37(15):2887–2891 (1988).
Bagasra, et al., J. Infect. Dis. 158(5):1084–1087 (1988).
Baba, et al., Antiviral Res. 9:335–343 (1988).
Scrip 1380, p. 24 (1989) Hoe/Bay 946 in AIDS.
PharmaProjects (1), Mar. 1, 1989.
Fauci, Proc. Natl. Acad. Sci. USA 89:9278–9283 (1986).
Palker, et al., Proc. Natl. Acad. Sci. USA 85:1932–1936 (Mar. 1988).
Nader, et al., Int. J. Biol. Macromol. 3(6):356–360 (1981).
Mitsuya, et al., Retroviruses in Human Lymphoma/Leukemia, M. Miwa, et al. (eds), Japan Sci. Soc. Press, Tokyo/VNU Science Press, Utrecht, pp. 277–288, 1985.
Sandstrom, et al., Drugs 34:372–390 (1987).
Putney, et al., UCLA Symp. Mol. Cell. Biol., New Ser., 84:357–367 (1988).
Tochikura, et al., J. AIDS 2(5):441–447 (1989).
Cardin, et al., Transactions of the Association of American Physicians vol. CII, 1989, pp. 101–109.
Scrip 1379, p. 21, Jan. 20, 1989.
Wagner, Arzneim.–Forsch./Drug Res. 39(I), Nr. I (1989), pp. 112–113.
Kolata, "AIDS Patients and Their Above–Ground Underground" N.Y. Times Jul. 10, 1988.
Lifson, et al., Science 232: 1123–1127 (May 30, 1986).
Sodroski, et al., Nature 322: 470–474 (Jul. 31, 1986).
Fauci *Proc. Natl. Acad. Sci. USA* 1986, 83, 9278–9283.
Sandström et al. *Drugs* 1987, 34, 372–390.
Bagasra et al. *J. Infect. Dis.* 1988, 158(5), 1084–1087.
Yamamoto et al. *Arch. of AIDS Res.* 1987, 11, 45–56.
Ito et al. *Antiviral Res.* 1987, 7, 361–367.
Nakashima et al. *Jpn. J. Cancer Res.* 1987, 78, 1164–1168.

*Primary Examiner*—Kathleen K. Fonda
*Attorney, Agent, or Firm*—T. Helen Payne

[57] ABSTRACT

Various peptides having affinity for sulfated polysaccharides such as heparin, dextran sulfate and Pentosan polysulfate are bound to resins and used in affinity chromatography to prepare anti-HIV sulfated polysaccharides.

11 Claims, 5 Drawing Sheets

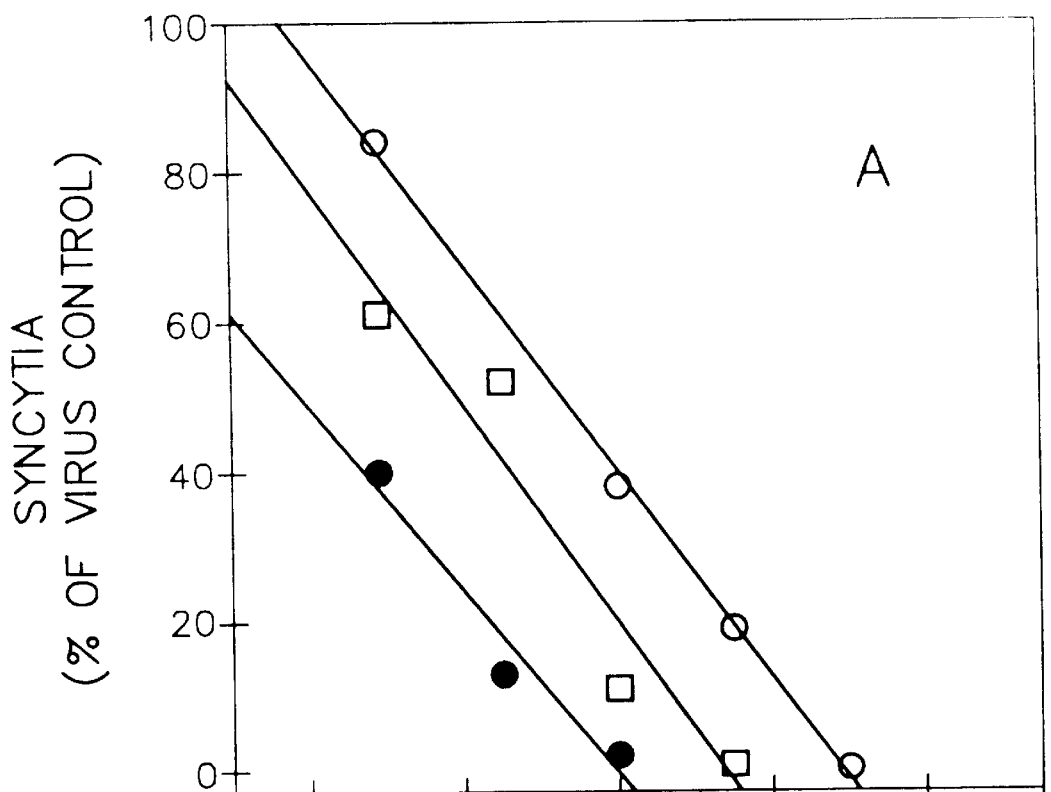
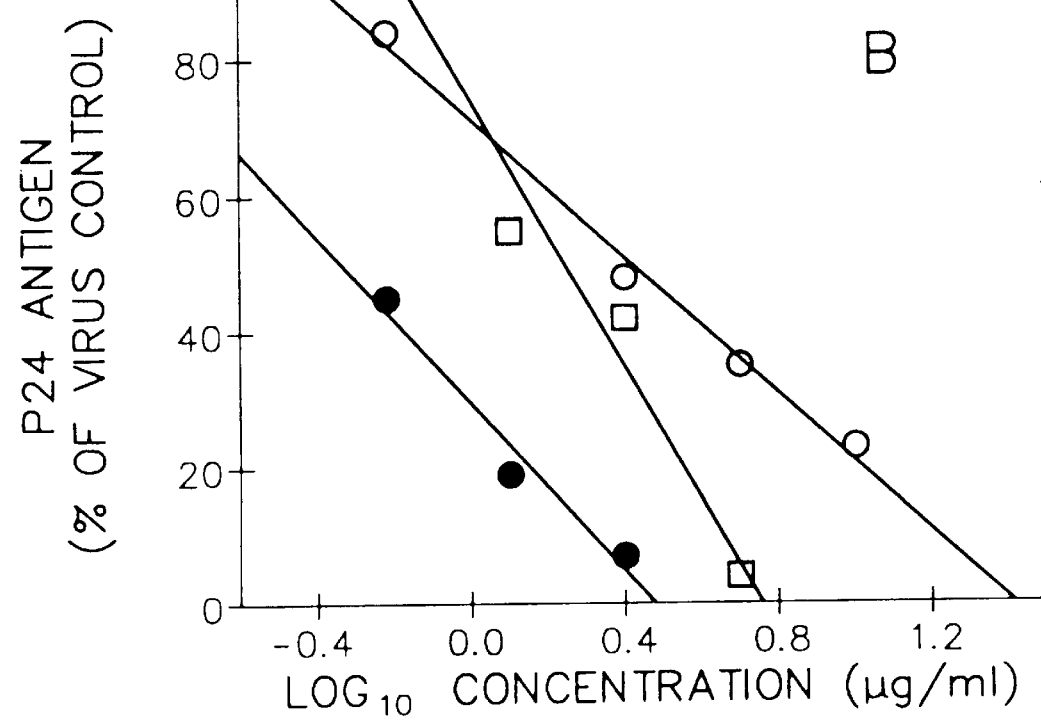
FIG. 2A
FIG. 2B

SULFATED POLYSACCHARIDE FRACTIONS HAVING ANTI-HIV ACTIVITY

This is a continuation of application Ser. No. 08/435,775 now abandoned, filed May 5, 1995, which is a Continuation of application Ser. No. 08/190,820, filed Feb. 2, 1994, now abandoned, which is a division of, application Ser. No. 08/001,370, filed Jan. 7, 1993, now abandoned, which is a Divisional of, application Ser. No., 07/821,130, filed on Jan. 14, 1992, now U.S. Pat. No. 5,272,261, issued Dec. 21, 1903 which is a Continuation of application Ser. No. 07/375,795, filed Jul. 5, 1989, now abandoned, which is a Continuation-in-part of application Ser. No. 07/295,856, filed Jan. 11, 1989, now abandoned, which is herein incorporated by reference.

This invention relates to anti-HIV sulfated polysaccharides and the isolation of these substances. Anti-HIV sulfated polysaccharides have valuable anti-human immunodeficiency virus activity and these substances are thus useful in the treatment of AIDS.

BACKGROUND OF THE INVENTION

A great deal of research is currently underway to develop treatments and cures for viral infections in humans and in animals. Notably the incidence of AIDS and ARC in humans is increasing at an alarming rate. The five year survival rate for those with AIDS is dispiriting and AIDS patients, whose immune systems have been seriously impaired by the infection, suffer from numerous opportunistic infections including Kaposi's sarcoma and Pneumocystis carinii pneumonia. No cure for AIDS is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (CDNA) from which a double stranded, proviral DNA is produced. This proviral DNA is then randomly incorporated into the chromosomal DNA of the host cell making possible viral replication by later translation of the integrated DNA containing the viral genome.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

The envelope protein of HIV is a 160 kDa glycoprotein. The protein is cleaved by a protease to give a 120 kDa external protein, gp 120, and a transmembrane glycoprotein, gp 41. The gp 120 protein contains the amino acid sequence that recognizes the receptor on CD4-positive human T-helper cells. Recently it was reported that the polysulfated polysaccharides dextran sulfate, carrageenans of sea algae, pentosan polysulfate, and heparin are highly specific inhibitors of HIV-1 replication in vitro. M. Ito, et al., (1987) Antiviral. Res. 7, 361–367. Baba et al., Antiviral Res. 9, 335–343 (1988). O. Yoshida (1988) Biochem. Pharmacol. 37, 2887–2981. R. Ueno and S. Kuno, (1987) Lancet i, 1379. The mechanism of this activity has been studied by Baba et al., (1988) Proc. Natl. Acad. Sci. USA, 85, 6132–6136. Another recent report indicates that antisera prepared against synthetic peptides corresponding to amino acid residues 307–330 and 303–321 in gp 120 inhibit HIV-induced syncytium formation. Rusche et al., Proc. Natl. Acad. Sci. USA 85, 2898–3202 (1988) and Palker et al., Proc. Natl. Acad. Sci USA 85, 1932–1936 (1988). Antibody binding to residues 303–330 in HIV gp 120 apparently interferes with the binding of the virus to the CD4 receptor and fusion with the plasma membrane.

Applicants have discovered that fractions of sulfated polysaccharides such as heparin, dextran sulfate and pentosan polysulfate, designated anti-HIV Heparin, anti-HIV dextran sulfate and anti-HIV-pentosan polysulfate, respectively, can be obtained by binding to a peptide corresponding to residues 301–324 of the HIV gp 120 protein and that anti-HIV Heparin, anti-HIV dextran sulfate, and anti-HIV pentosan polysulfate have significantly higher potency than unfractionated sulfated polysaccharides to prevent syncytium formation and appearance of viral P24 core antigen in the culture medium of HIV-infected CD4 cells and significantly reduces HIV infectivity. Anti-HIV sulfated polysaccharides can be used in the treatment of AIDS and ARC. The gp 120 peptide fragment is used in standard affinity chromatography to isolate anti-HIV sulfated polysaccharides.

SUMMARY OF THE INVENTION

An affinity chromatography is performed on crude heparin, dextran sulfate, or pentosan polysulfate using a resin-bound peptide of formula 1 (RP135).

NNTRKSIRIQRGPGRAFVTIGKIG

FORMULA 1

The fraction of sulfated polysaccharide which binds to the resin-bound RP135 peptide is useful in preventing syncytium formation in HIV-infected CD4+ cells and reduces HIV infectivity. The sulfated polysaccharide isolates of this invention are useful in the treament of AIDS and ARC.

EXPLANATION OF FIGURES

FIG. 2A. Dose-dependent inhibition of HIV-1 infection of JM cells by HRH (●); URH$_5$ (○) and MW 500,000 dextran sulfate (□) measured by virus-induced syncytia formation in supernatant culture fluid. Virus stock of the GB8 strain prepared from cell-free medium of acutely infected JM cells was diluted in growth medium (RPMI 1640, 10% fetal calf serum) containing different concentrations of test compound. After 15 minutes at room temperature, cells were added and virus adsorption carried out at this temperature for 2 hours to provide a multiplicity of infection (MOI) of 0.001 syncytial-forming units per cell. Infected cells were pelleted, washed three times in phosphate buffered saline, resuspended in fresh growth medium containing test compounds at appropriate concentrations and distributed into 24 well tissue culture plates. After 3 days incubation at 37° C., numbers of syncytia were scored in quadruple using an Olympus CK2 inverted microscope. At the same time, the supernatant culture fluid was sampled and clarified by centrifugation (2,000 rpm/5 minutes). The level of P24 antigen was determined by the Abbott core antigen Elisa test after treatment with 0.1% Triton X-100. Dose-response curves were plotted against $\log_{10}$ drug concentration and the 50% effective dose was computed for both tests after linear regression analysis.

FIG. 2B. Dose-dependent inhibition of HIV-1 infection of JM cells by HRH (●); URH$_5$ (○) and MW 500,000 dextran sulfated (□) measured by levels of P24 virion core antigen in supernatant culture fluid. Virus stock of the GB8 strain prepared from cell-free medium of acutely infected JM cells was diluted in growth medium (RPMI 1640, 10% fetal calf serum) containing different concentrations of test compound. After 15 minutes at room temperature, cells were added and virus adsorption carried out at this temperature for 2 hours to provide a multiplicity of infection (MOI) of 0.001 syncytial-forming units per cell. Infected cells were pelleted, washed three times in phosphate buffered saline, resuspended in fresh growth medium containing test compounds at appropriate concentrations and distributed into 24 well tissue culture plates. After 3 days incubation at 37° C., numbers of syncytia were scored in quadruple using an Olympus CK2 inverted microscope. At the same time, the supernatant culture fluid was sampled and clarified by centrifugation (2,000 rpm/5 minutes). The level of P24 antigen was determined by the Abbott core antigen Elisa test after treatment with 0.1% Triton X-100. Dose-response curves were plotted against $\log_{10}$ drug concentration and the 50% effective dose was computed for both tests after linear regression analysis.

DETAILED DESCRIPTION OF THE INVENTION

Figure 1:
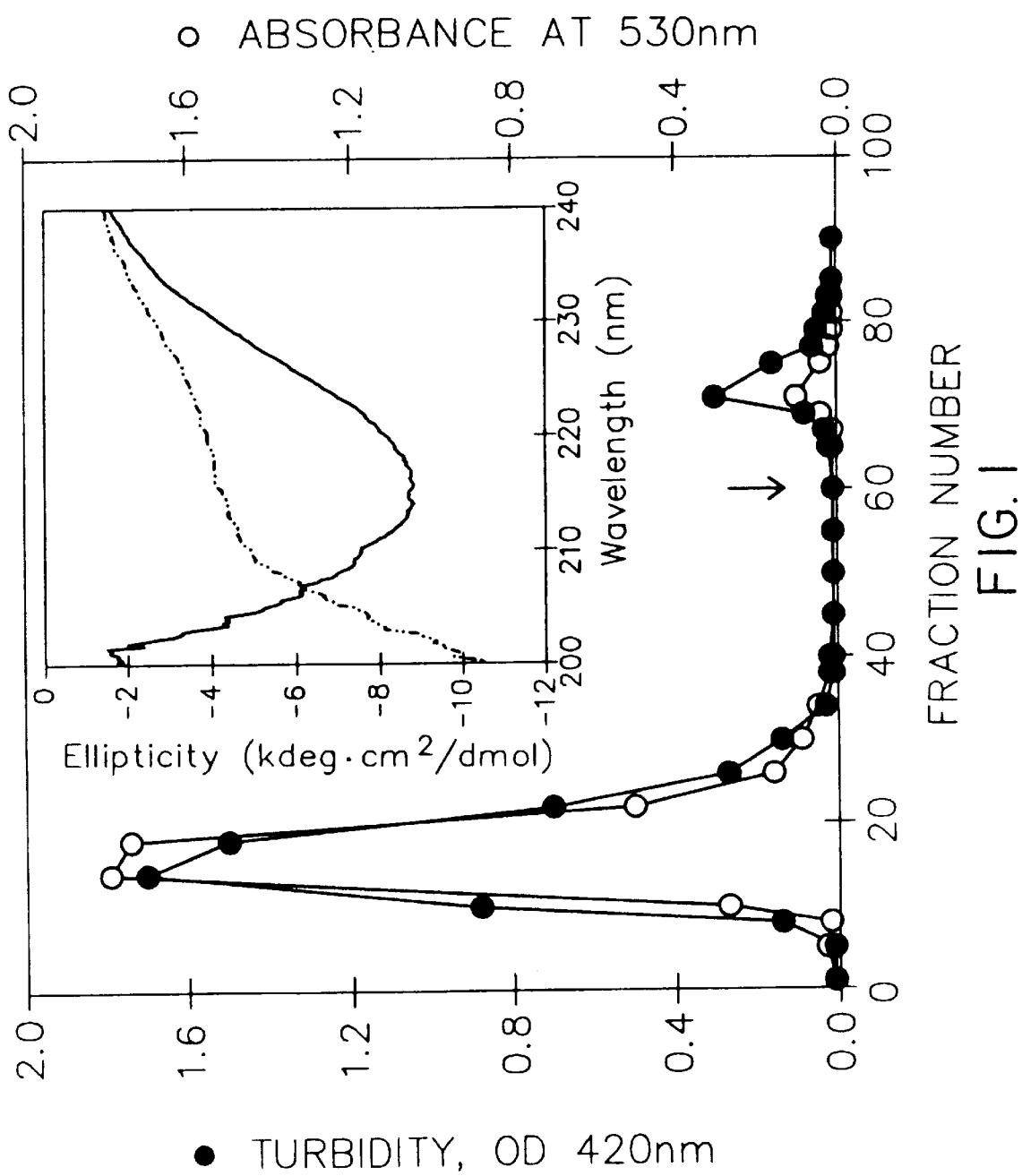
FIG. 1. Fractionation of a commercial heparin preparation (163 $\mu$/mg, USP)on RP-135-AffiGel-10. 200 mg (dry weight) of commercial grade heparin (HEPAR Industries) were applied to the peptide column (1×10 cm bed volume) equilibrated in 10 mM Hepes, pH 7.4, 0.05M NaCl. The column was extensively washed to remove the unbound or unreactive heparin (URH); 1 ml fractions were collected. The column was then eluted in equilibration buffer containing 1M NaCl (arrow) to obtain the high reactive heparin (HRH) bound to RP-135. Heparin was detected by turbidity with the protamine sulfate assay (●) as described. M. W. C. Hatton, L. R. Berry, E. Regoeczi, Thromb. Res. 13, 655-7 (1978). Briefly, 10 $\mu$l of various fractions were admixed with 100 $\mu$l of 1 mg/ml of protamine sulfate in $H_2O$ followed by the addition of 240 $\mu$l of column equilibration buffer. For the assay of 1M NaCl eluted fractions, 100 $\mu$l of sample were admixed with 250 $\mu$l of 1 mg/ml of protamine sulfate. Turbidity was measured at 420 nm. Uronic acid (0) was determined by the carbazole reaction. T. Bitter, H. M. Muir, Anal. Biochem. 4, 330 (1967). Inset: The effect of HRH (fractionated heparin) on the far ultraviolet circular dichroism (CD) of RP-135. The CD of RP-135 (100 $\mu$g/ml) in the absence (·–·) and presence (–) of HRH (60 $\mu$g/ml) in 10 mM Hepes, pH 7.4, 0.05M NaCl. Heparin induces a pronounced minimum at 225 nm attributable to a change in peptide conformation whereas heparin alone makes a negligible CD contribution.

Heparin is a heterogeneous group of straight-chain polysulfated mucopolysaccharides having an average molecular weight of 15,000 daltons. Heparin has significant biological and medical utility because of its anticoagulant activity. Commercial heparin is prepared from bovine lung or porcine intestinal mucosa and consists of polymers of various sugars, primarily α-L-iduronic acid 2-sulfate, 2-deoxy-2-sulfamino-α-D-glucose 6-sulfate, β-D-glucuronic acid, 2-acetamido-2-deoxy-α-D-glucose, and α-L-iduronic acid. The sugars are joined by glycosidic linkages and varying amounts of each sugar are present. Any of the commercially available heparin preparations may be used in the process of this invention.

Dextran sulfate is also a heterogeneous group of sulfated polysaccharides which can be prepared by the treatment of dextran with sulfuric acid and subsequently esterifying the intermediate product with chlorosulfonic acid. (See U.S. Pat. No. 2,715,091.) Typically dextran sulfate has an approximate molecular weight of about 7300 daltons and has up to three sulfate groups per glucose unit. Dextran, in turn, is a polyglucose substantially linked via the 1,6 positions of the glucopyranosyl unit in the alpha orientation. Dextrans and dextran sulfates have molecular weights of up to 500,000 daltons; however, dextran sulfate used in clinical applications is typically about 75,000 daltons.

Pentosan polysulfate is a polysaccharide of vegetable origin that is artifically sulfated (Raveux et al., *Bull. Soc. Chem. Fr.* 3: 2744–2749, (1966). Its average molecular weight varies typically between 3,000–6,000. The polysaccharide is composed of β-D-Xylo-pyranose with sulfated groups on C2 and C3. At every tenth residue, a 4-0-methyl-D-glucoconic acid residue with sulfated groups on C2 and C3 is associated in a lateral position in the chain.

Xylan polyhydrogen sulfate, an oligomer of xylopyranose with 1,8-sulfate residues per monomer. The substance Hoe/Bay 946 is one such xylan polyhydrogen sulfate being jointly developed by Hoechst AG and Bayer AG and it has a molecular weight of 6,000 Daltons and approximately 1/10 of the monosaccharide units are substituted by glucoronic acids. These sulfated polysaccharides can be prepared by reacting hemicellulose with SO3 in pyridine. Winkler, et al., Poster, IV International Conference on AIDS, Stockholm, 12-16.6.1988.

Chondroitin polysulfate (CPS) is a mucopolysaccharide with N-acetylchondrosine, acetylated disaccharide of 1,4 or 1,6 D-glucoronic acid and chondrosamine, as a repeating unit and with one sulfate group per disaccharide unit. CPS has a molecular weight of about 50,000. Dermatan sulfate, a related polysaccharide, contains iduronic acid instead glucoronic acid.

The sulfated polysaccharides of this invention can be in the neutral or salt form, such as the sodium, calcium or potassium salts.

The anti-HIV sulfated polysaccharides of this invention are that portion or fraction of whole heparin, dextran sulfate, pentosan polysulfate, xylan polyhydrogen sulfate, cardoran sulfate, or chondroitin polysulfate which exhibits affinity for the resin-bound RP-135 peptide of formula 1. It should be understood that while the RP-135 peptide has been used, other related peptides with up to 5 amino acid substitutions and those related peptides being extended on the amino or carboxy terminal ends or both as well as those related peptides being truncated on the amino or carboxy terminal ends, or both are expected to produce substantially similar results and applicants intend that the term RP135 peptide when used herein with regard to the preparation of anti-HIV sulfated polysaccharides will include such related peptides. In particular, Table 1 lists certain known variances of the RP-135 region of other HIV isolates. Peptides having these sequences as well as other RP-135 sequence variations may be substituted for the sequence of formula 1 in the process of this invention. In addition, other peptide regions in the gp 120/gp 41 that fulfill the criteria for heparin-binding, in that they bind heparin and other sulfated polysaccharides, and those peptide regions fitting the consensus sequence for heparin binding X—$B_2$—X—BX and X—$B_3$—$X_2$—B—X. A. D. Cardin and H. J. R. Weintraub, *Arteriosclerosis Vol. 9* p. 2132 (1989) are those intended (see Table 1).

The RP-135 peptide of formula 1 is covalently bound to a chromatography resin in the usual manner and the resin-bound RP-135 peptide is used to isolate anti-HIV Heparin by affinity chromatography in the conventional manner. See, for example, reference books such as C. R. Lowe and P. G. D. Dean "Affinity Chromatography", John Wiley and Sons, Inc., New York, 1974 and W. H. Southen, "Affinity Chromatography", John Wiley and Sons, Inc., New York, 1981.

| HIV Isolate | RP-135 Varient Sequence |
|---|---|
| III$_B$(BH10) | N N T R K S I R I Q R G P G R A F V T I G K I G |
| III$_B$(BH8)  | — — — — — K — — — — — — — — — — — — — — — — — — |
| RF     | — — — — — S   — T K — — — — — V I Y A T — Q I — |
| MN     | Y — K — — —   — H I — — — — — — Y — T K N I — |
| SC     | — — — T R S   — H I — — — — — — Y A T — D I — |
| WMJ-2  | — — V — R S   L S I — — — — — — R — R E   I — |
| LAV-MAL| — — — — R G   — H F — — — Q — L Y — T —   I V |
| SF-2   | — — — — — S   — Y I — — — — — — H — T — R I — |
| NY5    | — — — K — G   — A I — — — — T L Y A R E — I — |
| Z3     | SDKKI — Q S   — R I — — — K V — Y A K — G I T |

The resin must be insoluble in the solvents and buffers to be employed, it must be mechanically and chemically stable with good flow properties, it must be easily coupled to the formula 1 peptide, and it should have a large surface area accessible to the substrate to be absorbed. Examples of suitable resins are agarose, glass, cellulose, and the like, and dual-composition or chemically modified matrices, such as agarose-coated polyacrylamide, polyacrylic coated iron particles, glycidoxy-coated glasses and the like. Examples of water-insoluble resins are those having hydroxy, amine or carbonyl groups or halogen atoms. Examples of water-insoluble resins having hydroxy groups are polysaccharides (e.g., cellulose, agarose, cross-linked dextran, and the like), hydroxyalkylpolystyrene resins (e.g., hydroxyalkylated styrene-divinylbenzene copolymer, and the like), polyvinylalcohols or the like. Examples of the water insoluble resins having an amino group are aminoalkylpolysaccharides (e.g., aminoalkylcellulose such as aminoethylcellulose or aminohexylcellulose, aminoalkylagarose such as aminohexylagarose, and the like), p-aminobenzylpolysaccharides (e.g., p-aminobenzylcellulose, p-aminobenzylagarose, and the like), chitosan, aminoalkylpolystyrene resins (e.g., aminoalkylated styrene-divinylbenzene copolymer), polyacrylamides, and aminoalkylpolyacrylamides (e.g., aminoethylpolyacrylamide, and the like), and aminoalkyl-porous glasses (e.g., aminopropyl-porous glass, and the like). Examples of water-insoluble resins having a carboxyl group are carboxyalkylpolysaccharides (e.g., carboxyalkylagarose such as carboxyhexylagarose or carboxypentylagarose, carboxyalkylcellulose such as carboxymethylcellulose, carboxyalkyl-cross-linked dextran such as carboxymethyl-cross-linked dextran, and the like), carboxyalkylpolyacrylamides (e.g., carboxymethyl-polyacryl-amide, and the like), and carboxylic acid resins (e.g., acrylic acid-divinylbenzene copolymer, and the like). Examples of the water insoluble resins having a halogen atom are halogenoalkylpolystyrene resins (e.g., chloromethylated styrene-divinylbenzene copolymer). When a halogenoalkyl-polystyrene is used, it can be used as it is or it can be converted into a more activated form. For example, a halogenoalkylpolystyrene resin can be converted into a dialkylthioalkylpolystyrene resin having activity higher than that of the halogenoalklpolystyrene resin by reacting the resin with dialkyl sulfide.

When the resin has a hydroxy group, the resin can be activated, for example, with a cyanogen halide (such as cyanogen bromide), a monoepoxide (such as epichlorohydrin), a bioxirane (such as 1,4-bis(2,3-epoxypropoxy)butane), a halogenoacetyl halide (such as chloroacetyl chloride) and then the resulting activated resin is reacted with the peptide of formula 1, or the above activated resin is reacted with the free hydroxy group of the serine or threonine residue in the formula 1 peptide.

When the resin has an amino group,
(1) the resin can be activated with an aliphatic dialdehyde (e.g., glutaraldehyde) and the activated resin is then reacted with the peptide of formula 1 and then the resulting Schiff base is reduced with a reducing agent (e.g., sodium borohydride); or
(2) the resin can be activated with cyanuric halide (cyanuric bromide) and then the resulting activated resin is reacted with a peptide of formula 1; or
(3) the resin can be activated with a monoepoxide or bisepoxide and then the resulting activated resin reacted with the peptide of formula 1; or
(4) the resin can be activated by diazotization and then reacted with the peptide of formula 1.

When the resin has a carboxy group the resin can be reacted directly with the peptide of formula 1 to form an acid amide or by carbodiimide reaction linking free carboxyl to primary amine.

When the resin has a halogen atom the resin can be reacted directly with the peptide of formula 1 whereby a free amino, carboxy, or hydroxy group displaces the halogen from the resin.

Resins useful in carrying out the process of this invention include also a number of commercially available functionalized resins that can be conveniently used for preparing the resin bound peptide of the invention according to the techniques herein described or in any case known per se to one skilled in the art.

Examples of said matrices are: Sepharose® (Pharmacia Fina Chemicals, Uppsala, Sweden), Affi-Gel® 202, Affi-Gel-10 and 11 (Bio-Rad Inc., U.S.A.), Eupergit (Röhm Pharma, Weiterstadt, West Germany) and the like.

These functional derivatives are capable of directly linking to the peptide of formula 1.

In the resin bound peptide of the present invention the peptide is preferably bonded in an amount of about 2–300 $\mu$mol per 1 g (wet form of the resin bound peptide), but may be less or more depending on the coupling efficiency. "Wet-form" means wet-weight of resin bound peptide obtained after filtering its aqueous suspension.

The heparin containing solution to be fractionated preferably has a pH value of about 7–8.5. However, heparin solutions having a pH lower than 7 can also be used, at least in some instances, for example, when using epoxides or linking via water-soluble carbodiimide reaction. When fractionating a heparin solution with the resin bound peptide, either a continuous process using e.g., a column or a batchwise process, using the resin bound peptide "in bulk", can be employed.

For example, when a column is used the resin bound peptide may be packed in the column and washed with an ethanolamine solution to block off remaining or residual resin, functional groups not bonded to peptide, then washed with water to remove salts, and a buffer solution added to equilibriate the column at the optimal conditions for binding heparin or other sulfated polysaccharides to the peptide; then a heparin or other sulfated polysaccharide containing solution is passed through the column, the system is then rinsed with the above buffer solution, and finally the adsorbed heparin or other sulfated polysaccharide fraction of this invention is released from the resin by eluting, for instance, with an increasing salt gradient. The so obtained sulfated polysaccharide fraction is in a purified form, substantially free from many of the original contaminants.

On the other hand, when a batchwise process is carried out, a heparin or other sulfated polysaccharide containing solution is added to a suspension of the adsorbent, the resulting mixture is buffered at a pH between 2.5 and 8.5 and preferably at a pH value of 6.5–8.5 and stirred to selectively adsorb the sulfated polysaccharides on the adsorbent and then, after having recovered and rinsed the sulfated polysaccharide-bearing adsorbent, the sulfated polysaccharide is recovered in a purified form by releasing it from the adsorbent by means of a buffer containing a high salt concentration, typically 0.2–1.0M NaCl, for example, or at pH higher than 10, and preferably at a pH between 10 and 11.5 or by decreasing the pH. The ratio between the sulfated polysaccharide-containing solution and the adsorbent to be contacted depends on various parameters such as the total amount of sulfated polysaccharide in the solution, the specific adsorbent used, the selected working conditions, in particular the concentration of the sulfated polysaccharide solution and the kind and amount of contaminants. However, these range-finding operations are in the range of activity of the skilled technician on the basis of what is disclosed in the present application.

Anti-HIV sulfated polysaccharides can be used to prevent syncytium formation in cells infected with HIV-1 virus or other related viruses having gp120 surface protein. Anti-HIV sulfated polysaccharides can be used to treat AIDS and ARC and other diseases caused by the retrovirus HIV-1 or other related viruses having gp120 surface protein.

The amount of anti-HIV sulfated polysaccharide which is needed to prevent syncytium formation in HIV infected cells can be any effective amount. Experimentally, applicants have determined that anti-HIV sulfated polysaccharides when employed at a concentration of 10 $\mu$g/ml resulted in complete inhibition of syncytium formation as well as reduced the presence of P24 antigen, an indicator of viral replication, to below $3.0 \times 10^2$. The amount of anti-HIV sulfated polysaccharides to be administered in order to treat AIDS or ARC or other disease caused by HIV infection can vary widely according to the particular dosage unit employed, the period of treatment, the age and sex of the patient treated, the nature and extent of the disorder treated, and other factors well-known to those practicing the appropriate arts. Moreover anti-HIV sulfated polysaccharides can be used in conjunction with other agents known to be useful in the treatment of retroviral diseases and agents known to be useful to treat the symptoms of and complications associated with diseases and conditions caused by retroviruses. The anti-HIV effective amount of anti-HIV sulfated polysaccharides to be administered will generally range from about 15 mg/kg to 500 mg/kg. A unit dosage may contain from 25 to 500 mg of the sulfated polysaccharides, and can be taken one or more times per day. Anti-HIV sulfated polysaccharides can be administered with a pharmaceutical carrier using conventional dosage unit forms either orally or parenterally.

For oral administration anti-HIV sulfated polysaccharides can be formulated into solid or liquid preparations such as capsules, pills, tablets, troches, lozenges, melts, powders, solutions, suspensions, or emulsions. The solid unit dosage Forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The anti-HIV sulfated polysaccharides of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with, or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkyllmidazoline quarternary ammonium salts, as well as mixtures. The parenteral compositions of this invention will typically contain from about 0.5 to about 25% by weight of anti-HIV Heparin in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components t having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

EXAMPLES

The following examples illustrate various aspects of this invention.

Example 1

PREPARATION OF THE RP-135 PEPTIDE

The peptide RP135 (ref. PNAS 85:3198–3202 (1988)) was synthesized by solid-phase methods using an Applied Biosystems Model 430A synthesizer on 0.5 mmol of a Boc Gly(PAM)-resin (0.8 mmol/g); (Applied Biosystems). The $N^\alpha$-t-Boc-protected amino acids were double coupled as their preformed symmetrical anhydrides, first in N,N-dimethylformamide then in dichloro-methane using protocols supplied by the manufacturer. Asn, Arg and Gln were double coupled as their 1-hydroxybenzotriazole esters. An acetic anhydride capping step was included between each successive amino acid. The side chain protection was as follows: Lys(2-ClZ), Arg(Tos), Ser(Bzl), Thr(Bzl). The peptide was deprotected and cleaved from the resin (0.25 mmol) by treatment with liquid hydrofluoric acid (HF) containing 5% anisole at −5° C. (salt-ice bath) for 40 minutes. After removal of the HF invacuo, the peptide was extracted from the resin with 30% acetic acid followed by 30% acetonitrile. The filtrates were lyophilized and the residue dissolved in 6M urea. The peptide was purified on a Beckman 2 inch ×150 mm C18 column at 80 ml/min with a 20–25% linear gradient of acetonitrile in 0.1% trifluoroacetic acid over 15 min. The main peak was isolated and lyophilized leaving 137.9 mg of the desired product. Amino acid anlaysis (6N HCl, 48 hours, 106° C.) Asx 1.79(2); Thr 1.98(2); Ser 0.81(1); Glx 0.98(1); Pro 0.94(1); Gly 4.14(4); Ala 1.01(1); Val 1.09(1); Ile 3.85(4); Phe 0.98(1); Lys 2.07(2); Arg 3.75(4). FAB-MS (M+H)+: 2640.1 ±1 m.u. (calculated MW=2638.5).

Example 2

PREPARATION OF AFFIGEL-10 BOUND RP-135 PEPTIDE

To 10 ml AffiGel-10 (BIORAD) in 0.1M MOPS, pH 6.0–10.0 coupling buffer is added 100–300 mg of RP-135 in coupling buffer. The coupling reaction is carried out at 4° C. with gentle rocking for 4 hrs. Remaining active esters on the resin are blocked by adding 0.1 ml of 1M glycine ethyl ester (pH 8) or 0.1 ml of 1M ethanolamine HCl (pH 8) per ml of gel and then incubated for 1 hour. The resin is then transferred to a column and extensively washed with 0.01M Hepes, 0.05M NaCl, pH 7.4.

Example 3

ISOLATION OF ANTI-HIV HEPARIN BY AFFINITY CHROMATOGRAPHY USING AFFIGEL-10 BOUND RP-135 PEPTIDE

FIG. 1 shows the fractionation of a commercially obtained heparin preparation on RP-135-AffiGel-10. Approximately 2% of total heparin (as determined by uronic acid and dry weight) was retained by the peptide column and subsequently eluted with 1M NaCl. Five successive repassages of the unbound heparin ($URH_5$) yielded decreasing amounts of the bound or high reactive heparin (HRH) such that by the 5th passage no HRH was recovered. A control column made by coupling ethanolamine to AffiGel-10 did not yield any bound heparin. The inset of FIG. 1 shows that by CD analysis HRH increases the ordered structure of RP-135 (17% α-helix, 43% β-turn, 40% random coil). RP-135 in solution is predominantly random structure (17% α-helix, 13% B-turn, 70% random coil). Thus, upon binding heparin, RP-135 undergoes a change in peptide conformation characteristic of a specific interaction. These findings show that the heparin with highest affinity for RP-135 had been fractionated from crude commercial heparin. That crude heparin did not bind to ethanolamine Affigel-10 and was depleted of HRH by successive rechromatography over the peptide-column indicates a selective interaction of a specific subfractionation of heparin with RP-135. As such, the sequence represented by RP-135 in gp120 binds glycosaminoglycans.

TABLE 1

PUTATIVE gp120 HEPARIN BINDING REGIONS

| gp120 - | $^{165}$I S T S K R G K V Q K E Y A F F Y K |
| gp120 - (RP-135) | $^{306}$N N N T R K S I R I Q R G P G R A F |
| gp120 - | $^{477}$S E L Y K Y K V V K I E P L G V A P |
| gp120 - | $^{494}$P T K A K R R V V Q R E K R A V G I |

PUTATIVE gp41 HEPARIN BINDING REGIONS

| gp41 - | $^{227}$G E R D R D R D S I R L V N G S L A L |
| gp41 - | $^{271}$V E L L G R R G W E A L K Y W W N L |
| gp41 - | $^{325}$A Y R A I R H I P R R I R Q G L E R |

Table 1 shows other putative heparin-binding regions of gp120 and gp41 that function in binding glycosaminoglycans and other sulfated polysaccharides. These domains show a high positive charge density conforming to two types of consensus sequences for heparin binding X—B$_2$—X—B—X and X—B$_3$—X$_2$—B—X where B and X are basic and noncharged residues as previously defined by A. D. Cardin and H. J. R. Weintraub, *Arteriosclerosis* Vol. 9 (1989) p. 21–22). Synthetic peptides of these domains may be used in the same way as RP-135 to fractionate sulfated polysaccharides with increased inhibitory activity against HIV.

Example 4

ABILITY OF ANTI-HIV HEPARIN TO PREVENT SYNCYTIA FORMATION AND EXPRESSION OF P24 VIRAL CORE ANTIGEN USING JM CELLS AND GB8 VIRUS STRAIN

To show that the heparin that binds RP-135 blocks HIV infection, CD4$^+$ T-cells (JM) were exposed to a clinical isolate of HIV-1, GB8 (24). The virus was first incubated with HRH for 15 minutes and then the cells were added. After 2 hours adsorption, the virus inoculum was removed and the cells were washed three times to remove traces of input virus. Antiviral activity was determined after 3 days incubation by plotting the mean number of syncytia found in quadruple cultures against log$_{10}$ concentration of sulfated polysaccharide. The 50% effective dose [ED$_{50}$] of HRH for inhibition of syncytia was estimated as 0.3 μg/ml (FIG. 2A). This value compares with 2.2 and 1.5 μg/ml for URH$_5$ and dextran sulfate (M$_r$=500,000), respectively (FIG. 2A). The potency of HRH, URH$_5$ and dextran sulfate was also measured by assaying viral core antigen (P24 test-Abbott) in the supernatant fluid (FIG. 2B). ED$_{50}$ values of 0.4, 3.0, and 2.0 μg/ml were obtained for HRH, URH$_5$ and dextran sulfate respectively, a rank order identical to that determined by the syncytial assay. Subsequent experiments showed the antiviral activity of heparin with affinity for RP-135 was consistently 10-fold greater than unbound fractions and in every case greater than that obtained with high molecular weight dextran sulfate.

Example 5

ABILITY OF ANTI-HIV HEPARIN TO COMPLETELY BLOCK SYNCYTIA FORMATION AT 10 μg/ml USING JM CELLS AND GB8 VIRUS STRAIN

Figure 3A:
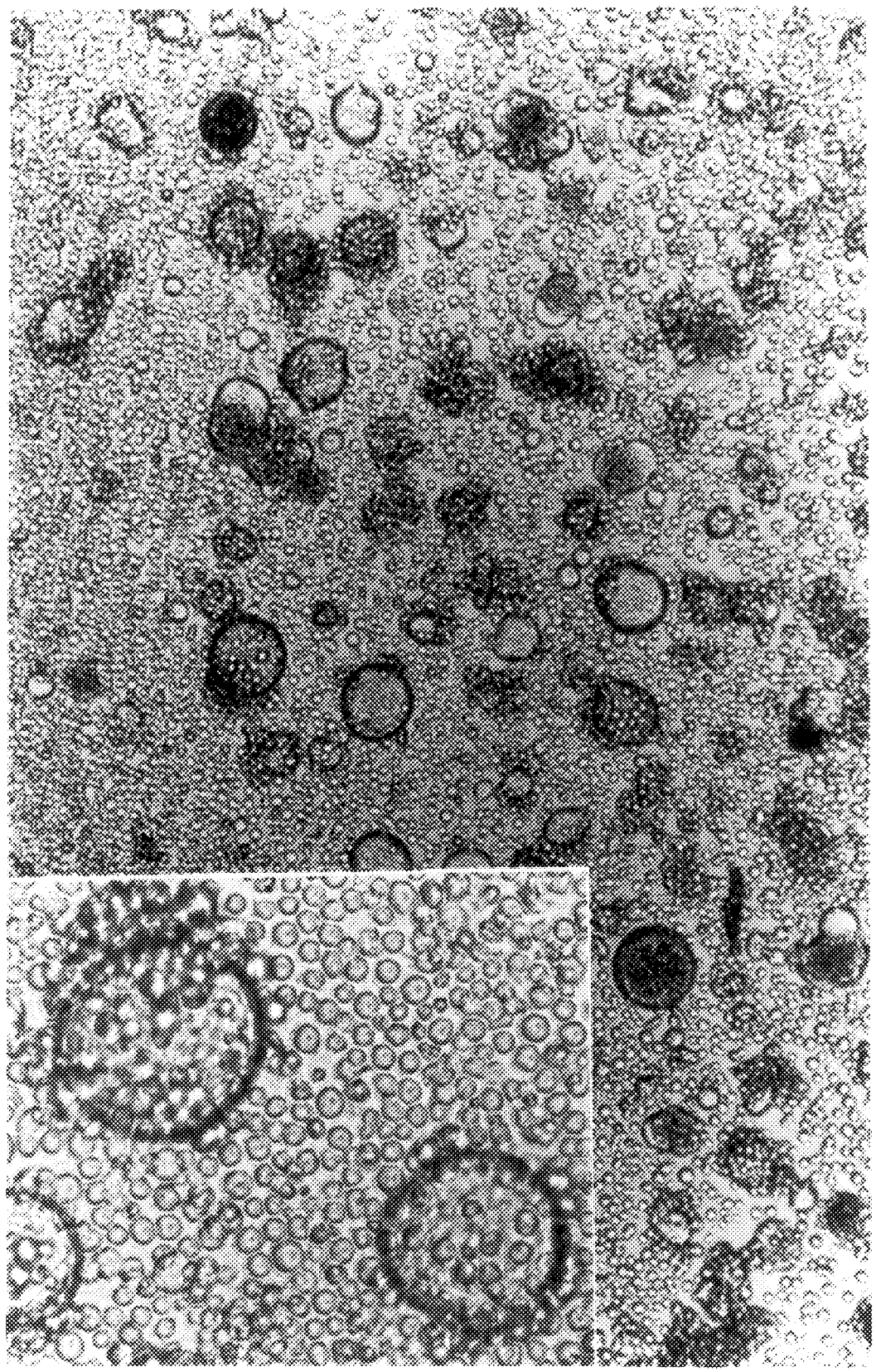
FIG. 3A. Photomicrographs of JM cells infected with the GB8 strain of HIV-1 and incubated in the absence of HRH for 3 days (see legend to FIG. 2 for methods). Numbers of syncytia induced after this period of infection remained linear to dilution (not shown). Total protection was provided by HRH at 10 μg/ml and cells were indistinguishable from uninfected control cells (not shown). Photography was carried out using an Olympus P7-10 AK automatic exposure system. Final magnification for main illustration and inset were ×220 and ×550, respectively.
Figure 3B:
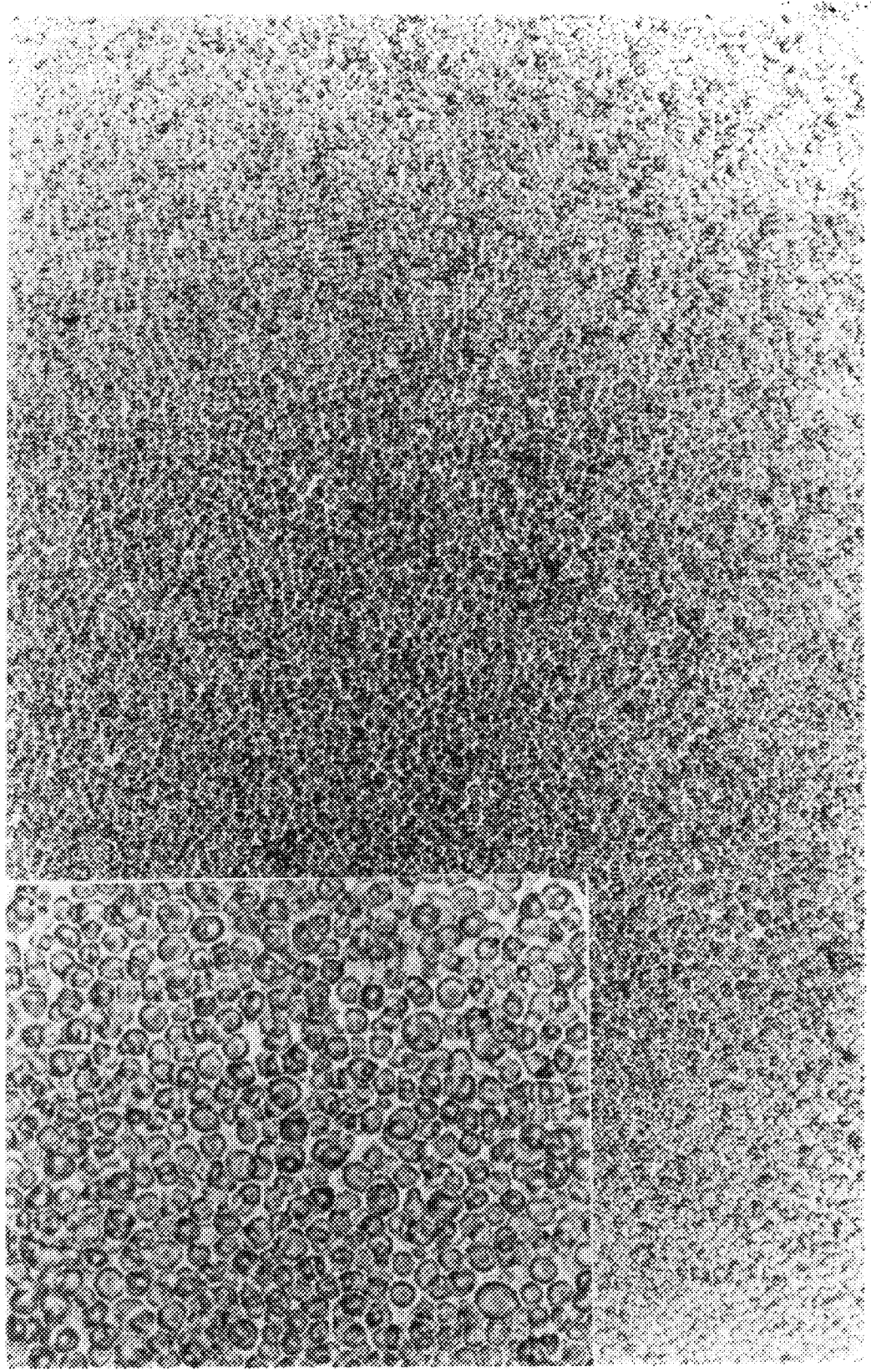
FIG. 3B. Photomicrographs of JM cells infected with the GB8 strain of HIV-1 and incubated in the presence of 10 μg/ml HRH for 3 days (see legend to FIG. 2 for methods). Numbers of syncytia induced after this period of infection remained linear to dilution (not shown). Total protection was provided by HRH at 10 μg/ml and cells were indistinguishable from uninfected control cells (not shown). Photography was carried out using an Olympus P7-10 AK automatic exposure system. Final magnification for main illustration and inset were ×220 and ×550, respectively.

FIG. 3A and 3B show photo-micrographs of infected cells cultured in the absence and presence of 10 μg/ml HRH, a concentration that gave complete protection against syncytia formation.

TABLE 2

RP-135; A PUTATIVE gp120 HEPARIN-BINDING REGION WITH SEQUENCE SIMILARITY TO THE HEPARIN-BINDING DOMAIN OF VITRONECTIN

[X-B-B-B-X-X-B-X]$^a$

| | | | | | | | | | |
|---|---|---|---|---|---|---|---|---|---|
| RP-135 | 307 | N N T R | K S I | R | I | Q | R G P | G | R A F | V T I G K I G |
| VITRONECTIN$^b$ | 353 | H R N R | K G Y | R | S | Q | R G H | S | R G R | N Q N S R R P |

$^a$Consensus sequence for heparin-binding where B is the probability of occurrance of a basic residue and X is a nonchanged residue.
$^b$Heparin-binding sequence of vitronectin according to Suzuki et al. Embo J. 4, 2519 (1985). The boxed areas denote regional similarities. Conservative substitutions are denoted by pairs of residues falling into the following groups: S, T, A, G, P; N, D, E, Q; R, K, H; M, I, L, V; F, Y, W.

Table 2 shows the heparin binding region of vitronectin and its similarity in sequence to RP-135. Consequently, vitronectin attached to Affi-Gel might also be used to obtain heparin or other sulfated polysaccharide fractions with high affinity for gp120/gp41 and higher anti-HIV activity.

Example 6

ABILITY OF ANTI-HIV HEPARIN TO PREVENT EXPRESSION OF P24 VIRAL CORE ANTIGEN BY DIFFERENT VIRAL STRAINS (GB8, RF AND III-B) AND CELLS (JM AND C8166)

Figure 4A:
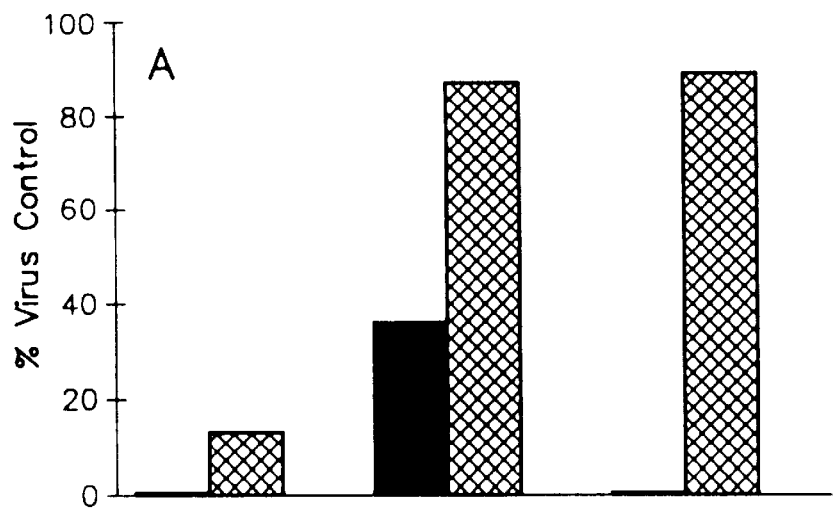
FIG. 4A. The relative effects of HRH, URH$_5$ and dextran sulfate (500,000) at 10 μg/ml (shaded) and 1 μg/ml (cross-hatched) were assessed against different strains of HIV. Levels of P24 antigen were measured in supernatant culture fluids of JM cells infected with the GB8 strain. Methods were as described in the legend to FIG. 2. The MOI of infection was determined between 0.01 and 0.001 infectious units per cell by an endpoint syncytial method. An increased antiviral effect was evident with HRH in all cases when compared to URH$_5$ or dextran sulfate.
Figure 4B:
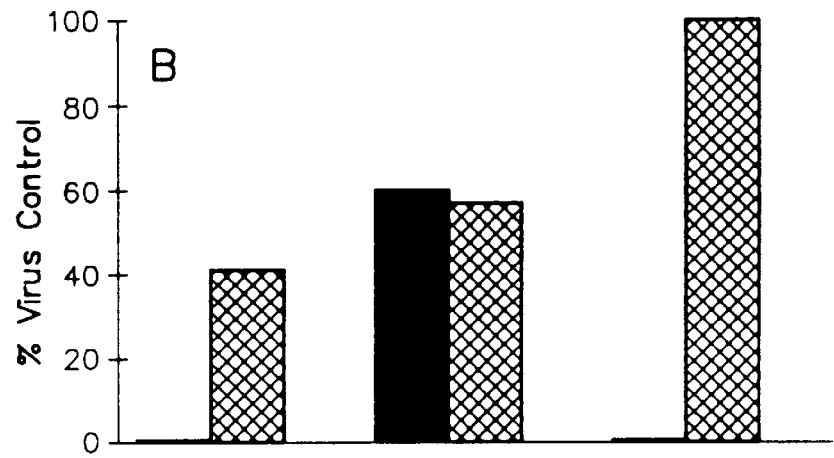
FIG. 4B. The relative effects of HRH, URH$_5$ and dextran sulfate (500,000) at 10 μg/ml (shaded) and 1 μg/ml (cross-hatched) were assessed against different strains of HIV. Levels of P24 antigen were measured in supernatant culture fluids of C8166 cells infected with the RF strain. Methods were as described in the legend to FIG. 2. The MOI of infection was determined between 0.01 and 0.001 infectious units per cell by an endpoint syncytial method. An increased antiviral effect was evident with HRH in all cases when compared to URH$_5$ or dextran sulfate.
Figure 4C:
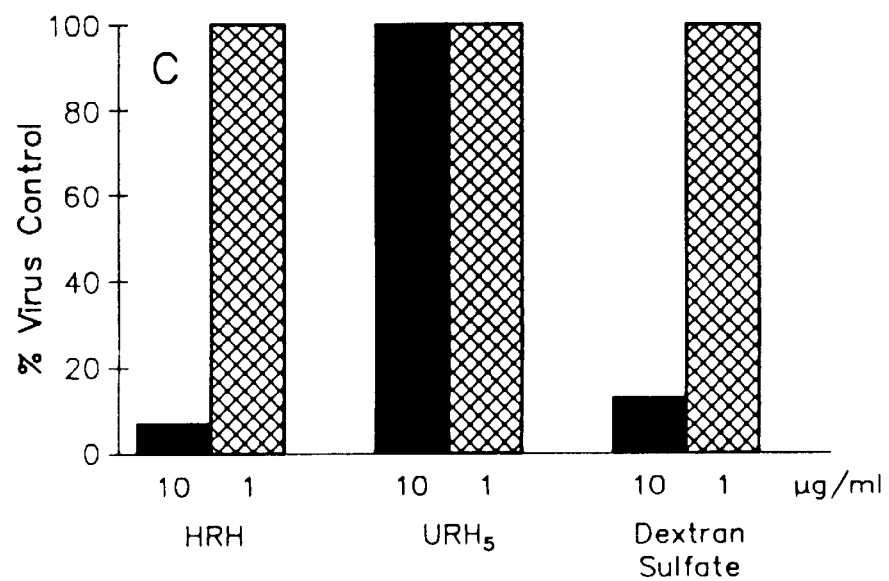
FIG. 4C. The relative effects of HRH, URH$_5$ and dextran sulfate (500,000) at 10 μg/ml (shaded) and 1 μg/ml (cross-hatched) were assessed against different strains of HIV. Levels of P24 antigen were measured in supernatant culture fluids of C8166 cells infected with the HTLV-IIIB strain. Methods were as described in the legend to FIG. 2 except HTLV-IIIB infected cells were sampled at 4 days postinfection. The MOI of infection was determined between 0.01 and 0.001 infectious units per cell by an endpoint syncytial method. An increased antiviral effect was evident with HRH in all cases when compared to URH$_5$ or dextran sulfate.

The protective effect of anti-HIV heparin (HRH) was confirmed in other experiments using the T-cell line C8166 infected with either prototype strain of HIV-l, RF or HTLV-IIIB. HRH demonstrated the highest anti-HIV potency (FIG. 4A–C). HRH, URH$_5$, and dextran sulfate were not toxic to these cells at concentrations of 100 µg/ml as determined by a tetrazolium reduction assay. However, HRH had a higher anticoagulant activity than URH$_5$ and dextran sulfate. At 10 µg/ml, clot times for HRH, URH$_5$ and unfractionated heparin were increased 2.4, 1.5, and 1.9 times, respectively, that of control plasma for HIV activity.

TABLE 3

ANTICOAGULANT PROPERTIES OF VARIOUS HEPARIN FRACTIONS

| SAMPLE | HEPARIN MASS[a] | CLOT TIME (SEC.) |
| --- | --- | --- |
| Control | — | 15.8 ± 0.3 (n = 8) |
| HRH[b] | 920 | 37.1 ± 2.7 (n = 10) |
|  | 460 | 20.0 ± 0.4 (n = 8) |
|  | 180 | 17.3 ± 0.3 (n = 8) |
| URH$_5$ | 920 | 23.5 ± 0.7 (n = 10) |
| Crude Heparin | 920 | 29.4 ± 0.9 (n = 10) |

[a]Measured as ng heparin drywt./100 µl plasma
[b]Purified by fractionating crude heparin on RP-135-AffiGel-10.

At 0.4 µg/ml (i.e., the ED$_{50}$ value) HRH had little detectable anti-clotting activity (not shown). Considering the anti-HIV-1 potency (ED$_{50}$≦0.35 µg/ml) of HRH it should be possible to administer heparin in vivo at concentrations that have minimal anticoagulant effects with significant anti-HIV-1 activity.

I claim:

1. A method of reducing synctium formation in a human immunodeficiency virus-infected CD4+ cell comprising contacting the cell with a fraction of sulfated polysaccharide purified by binding affinity to a peptide encoding a consensus sequence for heparin binding.

2. The method according to claim 1, wherein the consensus sequence is selected from the sequence encoding human immunodeficiency virus glycoprotein 120 or human immunodeficiency virus glycoprotein 41.

3. The method according to claim 2, wherein the consensus sequence is an RP-135 variant sequence.

4. The method according to claim 3, wherein the RP-135 variant sequence comprises

STSKRGKVQKEYAFFYK;

NNNTRKSIRIQRGPGRAF;

SELYKYKVVKIEPLGVAP;

PTKAKRRVVQREKRAVGI;

GERDRDRSIRLVNGSLAL;

VELLGRRGWEALKYWWNL; or

AYRAIRHIPRRIRQGLER.

5. The method according to claim 4, wherein the RP-135 variant sequence is NNNTRKSIRIQRGPGRAF.

6. The method according to claim 1, wherein the sulfated polysaccharide comprises heparin, dextran sulfate, pentosan polysulfate, cardoran sulfate, xylan polyhydrogen sulfate, chondroitin polysulfate or dermatan sulfate.

7. The method according to claim 6, wherein the consensus sequence is an RP-135 variant sequence.

8. The method according to claim 7, wherein the RP-135 variant sequence is NNNTRKSIRIQRGPGRAF.

9. The method according to claim 6, wherein the sulfated polysaccharide is heparin.

10. The method according to claim 9, wherein the consensus sequence is an RP-135 variant sequence.

11. The method according to claim 10, wherein the RP-135 variant sequence is NNNTRKSIRIQRGPGRAF.

* * * * *